(12) United States Patent
Huisman et al.

(10) Patent No.: US 8,748,139 B2
(45) Date of Patent: *Jun. 10, 2014

(54) MICROBIAL STRAINS AND PROCESS FOR THE MANUFACTURE OF BIOMATERIALS

(75) Inventors: Gjalt W. Huisman, San Carlos, CA (US); Laura Z. Luo, Laport, TX (US); Oliver P. Peoples, Arlington, MA (US)

(73) Assignee: Metabolix, Inc., Cambridge, MA (US)

( * ) Notice: Subject to any disclaimer, the term of this patent is extended or adjusted under 35 U.S.C. 154(b) by 1012 days.

This patent is subject to a terminal disclaimer.

(21) Appl. No.: 10/607,903

(22) Filed: Jun. 27, 2003

(65) Prior Publication Data

US 2004/0014197 A1    Jan. 22, 2004

Related U.S. Application Data

(60) Continuation of application No. 09/456,940, filed on Dec. 7, 1999, now abandoned, which is a division of application No. 09/281,363, filed on Mar. 30, 1999, now abandoned.

(60) Provisional application No. 60/079,938, filed on Mar. 30, 1998.

(51) Int. Cl.
  *C12P 7/52*     (2006.01)
  *C12P 21/06*    (2006.01)

(52) U.S. Cl.
  USPC ........................... 435/141; 435/69.1; 435/135

(58) Field of Classification Search
  USPC ................................................ 435/69.1, 91.2
  See application file for complete search history.

(56) References Cited

U.S. PATENT DOCUMENTS

| | | |
|---|---|---|
| 4,326,052 A | 4/1982 | Kang et al. |
| 4,336,334 A | 6/1982 | Powell et al. |
| 4,377,636 A | 3/1983 | Kang et al. |
| 4,385,126 A | 5/1983 | Chen et al. |
| 4,400,467 A | 8/1983 | Bauer et al. |
| 4,477,654 A | 10/1984 | Holmes et al. |
| 4,503,084 A | 3/1985 | Baird et al. |
| 4,786,598 A | 11/1988 | Lafferty et al. |
| 4,948,733 A | 8/1990 | Easson et al. |
| 4,977,089 A | 12/1990 | Kovacevic et al. |
| 5,059,536 A | 10/1991 | Page et al. |
| 5,096,819 A | 3/1992 | Page et al. |
| 5,225,227 A | 7/1993 | Yalpani |
| 5,229,158 A | 7/1993 | Yalpani |
| 5,245,023 A | 9/1993 | Peoples et al. |
| 5,266,470 A | 11/1993 | Senior et al. |
| 5,290,910 A | 3/1994 | Shiotani et al. |
| 5,292,860 A | 3/1994 | Shiotani et al. |
| 5,302,525 A | 4/1994 | Groleau et al. |
| 5,334,520 A | 8/1994 | Dennis |
| 5,344,769 A | 9/1994 | Witholt et al. |
| 5,346,817 A | 9/1994 | Akiyama et al. |
| 5,354,671 A | 10/1994 | Pollock |
| 5,364,778 A | 11/1994 | Byrom |
| 5,371,002 A | 12/1994 | Dennis et al. |
| 5,434,062 A | 7/1995 | Groleau et al. |
| 5,472,870 A | 12/1995 | Pollock et al. |
| 5,512,456 A | 4/1996 | Dennis |
| 5,518,907 A | 5/1996 | Dennis |
| 5,563,051 A | 10/1996 | Ellwood et al. |
| 5,663,063 A | 9/1997 | Peoples et al. |
| 5,679,556 A | 10/1997 | Homma et al. |
| 5,705,368 A | 1/1998 | Murofushi et al. |
| 5,792,630 A | 8/1998 | Tonouchi et al. |
| 5,821,109 A | 10/1998 | Ben-Bassat et al. |
| 5,854,034 A | 12/1998 | Pollock et al. |

FOREIGN PATENT DOCUMENTS

| | | |
|---|---|---|
| EP | 0 176 320 | 4/1986 |
| WO | WO 91/13207 | 9/1991 |
| WO | WO 92/18553 | 10/1992 |
| WO | WO 92/21708 | 12/1992 |
| WO | WO 94/10289 | * 5/1994 |
| WO | WO 94/24302 | 10/1994 |
| WO | WO 95/10614 | 4/1995 |
| WO | WO 95/34643 | 12/1995 |
| WO | WO 96/00263 | 1/1996 |
| WO | WO 96/17369 | 6/1996 |

OTHER PUBLICATIONS

Boynton et al., Applied and Environmental Microbiology, vol. 65, No. 4, pp. 1524-1529, Apr. 1999.*
Biedermann, et al., "Fermentation studies of the secretion of Serratia marcescens nuclease by *Escherichia coli*", *Appl. Environ. Microbiol.*, 56(6):1833-8 (1990).
Ahrenholtz, et al., "A conditional suicide system in *Escherichia coil* based on the intracellular degradation of DNA," *Appl. Environ. Microbiol.* 60(10): 3746-3751 (1994).
Atkinson & Mavituna, *Biochemical Engineering and Biotechnology Handbook*, 2nd ed., Stockton Press: New York (1991).
Chen, et al., "Bacterial alginate produced by a mutant of *Azobacter vinelandii*," *Appl. Environ. Microbiol.* 49: 543-546 (1985).
Chen, et al., "Anaerobic degradation of veratrylglycerol—β—guaiacyl ether and guaiacoxyacetic acid by mixed rumen bacteria," *Appl. Environ. Microbiol.* 50(6): 1451-1456 (1985).
Delest, "Fermentation technology of microbial polysaccharides," in *Gums and Stabilisers for the Food Industry 5*, (Phillips, et al., eds.) IRL Press: New York, pp. 301-313 (1989).

(Continued)

*Primary Examiner* — Richard Hutson
(74) *Attorney, Agent, or Firm* — Pabst Patent Group LLP

(57) ABSTRACT

DNA constructs and genetically engineered microbial strains constructed using these DNA constructs, which produce a nuclease enzyme with specificity for DNA and/or RNA, are provided. These strains secrete nuclease into the periplasm or growth medium in an amount effective to enhance productivity and/or recovery of polymer, and are particularly suited for use in high cell density fermentation processes. These constructs are useful for modifying microbial strains to improve production and recovery processes for polymers such as intracellular proteins, such as enzymes, growth factors, and cytokines; for producing polyhydroxyalkanoates; and for producing extracellular polysaccharides, such as xanthan gum, alginates, gellan gum, zooglan, hyaluronic acid and microbial cellulose.

10 Claims, No Drawings

(56) References Cited

OTHER PUBLICATIONS

DOI, "Microbial synthesis, physical properties, and biodegradability of polyhydroxyalkanoates," *Macromol. Symp.* 98: 585-599 (1995).

Dougherty & Van De Rijn, "Molecular characterization of *has*A from an operon required for hyaluronic acid synthesis in group A streptococci," *J. Biol. Chem.* 269(1): 169-175 (1994).

Fialho, et al., "Conjugal transfer of recombinant plasmids into gellan gum-producing and non-producing variants of *Pseudomonas elodea* ATCC 31461," *Lett. Appt. Microbiol.* 12(3): 85-87 (1991).

Hassler & Doherty, "Genetic engineering of polysaccharide structure: production of variants of xanthan gum in *Xanthomonas campestris*," *Biotechnol. Prog.* 6(3): 182-187 (1990).

Herrero, et al., "Transposon vectors containing non-antibiotic resistance selection markers for cloning and stable chromosomal insertion of foreign genes in gram-negative bacteria," *J. Bacteriol.* 172: 6557-6567 (1990).

Kennedy & Bradshaw, "Production, properties, and applications of xanthan," *Prog. Ind. Microbiol.* 19: 319-371 (1984).

Le Loir, et al., "Direct screening of recombinants in gram-positive bacteria using the secreted *Staphylococcal* nuclease as a reporter," *J. Bacteriol.* 176(16): 5135-5139 (1994).

Lee & Chang, "Production of poly(hydroxyalkanoic acid)," *Adv. Biochem. Eng. Biotechnol.* 52: 27-58 (1995).

Liebl, et al., "Expression, secretion, and processing of *Staphylococcal* nuclease by *Corynebacterium glutamicum*," *J. Bacteriol.* 174(6): 1854-1861 (1992).

Miller, ed., *Methods in Enzymology: Bacterial Genetic Systems*, vol. 204, Academic Press: New York (1991).

Miller, et al., "Secretion and processing of *Staphylococcal* nuclease by *Bacillus subtilis*," *J. Bacteriol.* 169(8): 3508-3514 (1987).

Peoples, et al., "Poly-β-hydroxybutyrate (PHB) biosynthesis in *Alcaligenes eutrophus* H16. Identification and characterization of the PHB polymerase gene (phbC)," *Biol. Chem.* 264(26):15298-15303 (1989).

Peoples & Sinskey, "Fine structural analysis of the *Zoogloea ramigera phbA-phbB* locus encoding β-ketothiolase and acetoacetyl-CoA reductase: nucleotide sequence of *phbB*," *Mol. Microbiol.* 3(3): 349-357 (1989).

Poirier, et al., "Production of polyhydroxyalkanoates, a family of biodegradable plastics and elastomers, in bacteria and plants," *Bio/Technol.* 13: 142-150 (1995).

Pollock, "Gellan-related polysaccharides and the genus *Sphingomonas*," *J. Gen. Microbiol.* 139:1939-1945 (1993).

Sambrook, et al., *Molecular Cloning, A Laboratory Manual*, $2^{nd}$ ed., Cold Spring Harbor Laboratory Press: New York (1992).

Shortle, "A genetic system for analysis of *Staphylococcal* nuclease," *Gene* 22(2-3):181-189 (1983).

Spratt, et al., "Kanamycin-resistant vectors that are analogues of plasmids pUC8, pUC9, pEMBL8, and pEMBL9," *Gene* 41(2-3): 337-342 (1986).

Van Der Kooij, et al., "Growth of *Pseudomonas aeruginosa* in tap water in relation to utilization of substrates at concentrations of a few micrograms per liter," *Appl. Environ. Microbiol.* 44(5): 1086-1095 (1982).

Wells, "Extracellular microbial polysaccharides—a critical overview," in *Extracellular Microbial Polysaccharides* (Sanford, et al., eds.) ACS: Washington, DC, pp. 299-313 (1977).

Williams & Peoples, "Biodegradable plastics from plants," *CHEMTECH* 26: 38-44 (1996).

\* cited by examiner

SEQUENCE LISTING

<160> NUMBER OF SEQ ID NOS: 5

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:
      oligonucleotide primer SNS-Up

<400> SEQUENCE: 1
ttctctagaa ttcaggaggt ttttatggct atcagtaatg tttcg                45

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer SNS-Dn

<400> SEQUENCE: 2
gccggtacct tattgacctg aatcagcgtt g                               31

<210> SEQ ID NO 3
<211> LENGTH: 684
<212> TYPE: DNA
<213> ORGANISM: Staphylococcus aureus
<220> FEATURE:
<221> NAME/KEY: gene
<222> LOCATION: (1)..(684)
<223> OTHER INFORMATION: Staphylococcus aureus Nuclease Gene

<400> SEQUENCE: 3
gaattcagga ggttttatg tatggcaatt gtttcaatat tacttatagg gatggctatc      60
agtaatgttt cgaaagggca atacgcaaag aggttttct ttttcgctac tagttgctta    120
gtgttaactt tagttgtagt ttcaagtcta agtagctcag caaatgcatc acaaacagat    180
aacggcgtaa atagaagtgg ttctgaagat ccaacagtat atagtgcaac ttcaactaaa    240
aaattacata agaacctgc gactttaatt aaagcgattg atggtgatac ggttaaatta    300
atgtacaaag gtcaaccaat gacattcaga ctattattgg ttgatacacc tgaaacaaag    360
catcctaaaa aggtgtagaa gaaatatggt cctgaagcaa gtgcatttac gaaaaaaatg    420
gtagaaaatg caaagaaaat tgaagtcgag tttgacaaag gtcaaagaac tgataaatat    480
ggacgtggct tagcgtatat ttatgctgat ggaaaaatgg taaacgaagc tttagttcgt    540
caaggcttgg ctaaagttgc ttatgtttac aaacctaaca atacacatga caacattta    600 agaaaaagtg aagcacaagc gaaaaaagag aaattaaata tttggagcga agacaacgct    660
gattcaggtc aataaggtac cggc                                           684

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:
      oligonucleotide primer linkK1

<400> SEQUENCE: 4
tgtctgctta cataaacagt aatacaaag                                  29

-continued

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer linkK2

<400> SEQUENCE: 5
atttattcaa caaagccgcc                                              20
```

MICROBIAL STRAINS AND PROCESS FOR THE MANUFACTURE OF BIOMATERIALS

CROSS-REFERENCE TO RELATED APPLICATIONS

This is a continuation of U.S. Ser. No. 09/456,940 filed on Dec. 7, 1999 which is a divisional of Ser. No. 09/281,363, filed on Mar. 30, 1999, now abandoned, which claims priority to U.S. Provisional application Ser. No. 60/079,938, filed Mar. 30, 1998.

BACKGROUND OF THE INVENTION

The present invention is generally in the field of genetically engineered bacterial systems for the enhanced production and recovery of polymers such as intracellular proteins, polyhydroxyalkanoate materials, and extracellular polysaccharides.

Microbial fermentations are used for the manufacture of a large number of pharmaceutical and industrial products, including antibiotics, organic acids, amino acids, proteins, vitamins, polymers such as polyhydroxyalkanoates, and polysaccharides (Atkinson & Mavituna, "Biochemical Engineering and Biotechnology Handbook," $2^{nd}$ edition, (Stockton Press, USA 1991)) Increased productivity and recovery of more highly purified product are major areas of development to increase profitability. For many of these products, the industry trend generally is towards higher cell density fermentations to increase productivity. Cell densities in excess of 100 g/L are routinely achieved. Decreasing overall fermentation process costs by increasing the recovery of the product from the cell biomass or, in some cases, from the medium, is another means of increasing productivity.

Polyhydroxyalkanoates (PHAs) are biodegradable and biocompatible thermoplastic materials, produced from renewable resources, with a broad range of industrial and biomedical applications (Williams & Peoples, *CHEMTECH* 26:38-44 (1996)). A number of bacterial strains and fermentation processes have been described for the production of PHAs, such as described, for example, in Lee & Chang *Advances in Biochemical Engineer Biotechnology,* 52:27-58 (1995); Poirier et al., *Bio/Technology* 13:142-50 (1995); Doi, *Macromol. Symp.* 98:585-99 (1995). PHA production methods using specific bacterial strains are described in U.S. Pat. No. 4,477,654 to Holmes et al., U.S. Pat. No. 5,364,778 to Byrom, and U.S. Pat. No. 5,266,470 to Senior et al. (using *Ralstonia eutropha* (formerly *Alcaligenes eutrophus*) from carbohydrates); U.S. Pat. No. 5,346,817 to Akiyama et al. (using *Ralstonia eutropha* strains grown on fatty acids); U.S. Pat. No. 4,336,334 to Powell et al. (using *Methylobacterium organophilum*); U.S. Pat. No. 5,302,525 and U.S. Pat. No. 5,434,062 to Groleau et al. (using *Methylobacterium extorquens*); U.S. Pat. No. 5,292,860 to Shiotani et al. (using *Aeromonas* strains grown on fatty acids); U.S. Pat. No. 5,059,536 and U.S. Pat. No. 5,096,819 to Page et al. (using *Azotobacter vinelandii*); U.S. Pat. No. 4,786,598 to Lafferty (using *Alcaligenes latus*); U.S. Pat. No. 5,344,769 to Witholt et al. and U.S. Pat. No. 5,290,910 to Shiotani et al., PCT WO 92/18553 and PCT WO 92/21708 (using *Pseudomonas putida*); U.S. Pat. No. 5,245,023 to Peoples et al., U.S. Pat. No. 5,334,520 to Dennis, U.S. Pat. No. 5,371,002 to Dennis et al., U.S. Pat. No. 5,512,456 to Dennis, U.S. Pat. No. 5,518,907 to Dennis et al., and U.S. Pat. No. 5,663,063 to Peoples et al. (using transgenic *Escherichia coli*).

PHAs accumulate inside the microbial cells as discrete granular inclusions which although amorphous in nature are water insoluble. Recovery of PHAs from the cells following fermentation can be accomplished by any of several methods, including (1) solvent extraction; (2) chemical destruction of all non-PHA biomass using hypochlorite, hydrogen peroxide or ozone treatment; and (3) milder processing involving cell disruption, enzyme treatment, and washing. In the latter process, it is possible to retain the PHA granules in the amorphous state and use the washed granule suspension as a latex. It is necessary to lyse PHA-containing cells in order to obtain a PHA latex from the cells using an aqueous process. Efforts have been made to reduce the viscosity of the lysate. For example, U.S. Pat. No. 4,910,145 to Holmes et al. describes an aqueous process for the extraction of PHA from bacterial biomass, which uses a heat treatment step at 150° C. to reduce the viscosity of the lysate. PCT WO 94/24302 and PCT WO 94/10289 teach the use of hydrogen peroxide treatment to degrade the nucleic acid as a means to reduce viscosity. The addition of nucleases to cell lysates to reduce viscosity and enhance further processing also is generally known. This approach, however, is too expensive to use for commodity fermentation products involving high cell density fermentations.

Fermentation processes are widely used for the manufacture of enzymes and other bioactive proteins. In many cases, recovery can be improved by the addition of nuclease to the crude cell lysates to degrade nucleic acid. Advantageously, this approach also completely degrades DNA, which effectively eliminates the possible spread of antibiotic resistance markers or other genetic elements. As in the case of the PHAs, however, the process of adding exogenous nucleases is expensive.

Microbial polysaccharides are produced by fermentation of a number of different microorganisms. (Delest, P. 1989, pp. 301-313. Fermentation technology of microbial polysaccharides in Gums and Stabilisers for the Food Industry 5, Phillips, G. O., Wedlock, D. J. and Williams, P. A. eds. IRL Press at Oxford University Press, New York). For example, *Xanthomonas* strains are used commercially for the production of xanthan gum (Kennedy & Bradshaw, *Prog. Ind. Microbiol.* 19:319-71 (1984)), and have been subjected to genetic engineering techniques (Hassler & Doherty, *Biotechnol. Prog.* 6:182-87 (1990)). During this and similar fermentations, the viscosity of the medium increases dramatically as the extracellular polysaccharide is produced. Accordingly and in order to achieve good mixing in the fermenter, the mixer requires additional energy. The resulting increased shear can cause some cell lysis to occur, which releases nucleic acid into the medium. This nucleic acid is difficult to remove and presents a significant product quality problem, especially in use of the polysaccharides in biomedical applications, reducing the efficiency of separation processes, such as chromatography, crystallization, precipitation, centrifugation, and filtration.

It is therefore an object of this invention to provide improved methods of production and recovery using fermentation processes, especially those using high cell densities of polyhydroxyalkanoates, polysaccharides, and other intracellular and extracellular components.

It is another object of this invention to provide improved microbial strains for use fermentation processes, particularly those in which cell lysis or high cell densities occurs, or which results in high viscosity.

SUMMARY OF THE INVENTION

DNA constructs and genetically engineered microbial strains constructed using these DNA constructs, which produce a heterologous or modified homologous nuclease enzyme with specificity for DNA and/or RNA, have been developed. The heterologous nuclease can be obtained from another organism, engineered to increase enzyme activity, or homologous nucleases in the same strains mutated and then selected using assays for nuclease activity to select those bacteria expressing nucleases with enhanced activity. These strains secrete nuclease into the periplasm or growth medium in an amount effective to enhance recovery of the polymers and are particularly suited for use in high cell density fermentation processes. Exemplary polymers include intracellular proteins, such as enzymes, growth factors, and cytokines; polyhydroxyalkanoates; and polysaccharides, such as xanthan gum, alginates, gellan gum, zooglan, hyaluronic acid and microbial cellulose.

DETAILED DESCRIPTION OF THE INVENTION

Methods have been demonstrated for improving the fermentation and recovery process for microbial fermentation products by using strains which secrete a nuclease during the fermentation process wherein the nuclease itself is not the desired fermentation product. Methods for genetically engineering strains to secrete nucleases useful in this method are disclosed. In one embodiment a strain which does not express a suitable nuclease is genetically engineered to express an heterologous nuclease with sufficient activity to obtain the desired process improvement. In a second embodiment, a strain which expresses a nuclease but at insufficient activity to obtain the desired process improvement is genetically modified to express sufficient nuclease using the isolated nuclease gene from that strain and the methods described herein. In a third embodiment, a strain which expresses a suitable nuclease from a heterologous or homologous nuclease gene is mutated and mutants expressing sufficient levels of nuclease selected to obtain the desired process improvement

DEFINITIONS

The term "enhance" refers to an improved fermentation process wherein nucleic acid released by cell lysis during the fermentation is degraded by the nuclease, in an amount preventing viscosity increases, which can result in foaming, poor mixing and greater energy required for mixing. The term enhanced also refers to an improved recovery process wherein, in a process in which the desired product is produced intracellularly and requires cell lysis for recovery, nucleic acid released by cell lysis during the fermentation is degraded following the cell lysis step, in an amount preventing viscosity increases and facilitating the recovery steps which may include centrifugation filtration, precipitation etc.

The phrase "heterologous nuclease gene" refers to a nuclease gene isolated from a host other than the strain to be improved.

The phrase "homologous nuclease gene" refers to a nuclease gene isolated from the host to be improved. This gene may be further modified to improve the activity of the nuclease.

Nucleases and Genes Encoding Nucleases

Nucleases and genes encoding nucleases which are suitable for use in the methods described herein can be obtained from a number of sources. As used herein, "heterologous" nucleases are expressed from nucleic acid encoding the nucleases, wherein the nuclease has been obtained from an organism other than the one in which it is inserted to enhance polymer production and/or recovery; or where the organism is mutated and screened for enhanced nuclease activity. Enhanced nuclease activity can be obtained where the amount of nuclease, or the specific activity or substrate specificity of the nuclease, are increased.

Nucleases are secreted by a broad range of microorganisms and some of the corresponding genes have been cloned and characterized. Sources of nuclease genes include *S. marcescens* (GenBank Acc. No. M19495), *Anabaena* PCC7120 (GenBank Acc. No. X64706), *Bacillus subtilis* (GenBank Acc. No. U66480), *Staphylococcus hyicus* (GenBank Acc. No. L23973), *Staphylococcus intermedius* (GenBank Acc. No. X67678), *Escherichia coli* (GenBank Acc. No. X55818), *Shigella flexneri* (GenBank Acc. No. U30471), *Methanobacterium thermoautotrophicum* (GenBank Acc. No. AE000833), and *Methanococcus jannaschii* (GenBank Acc. No. U67584).

Preferably, the nuclease cleaves both ribonucleic acid (RNA) and deoxyribonucleic acid (DNA). The nuclease preferably is active over a wide temperature range and pH range. The nuclease also preferably is tolerant to the presence of processing additives, such as salts, surfactants, and stabilizers. Following cell lysis and an incubation period to allow the nuclease to degrade the nucleic acid, it is preferable that the nuclease be readily removable, for example, by protease digestion, chromatography, filtration or centrifugation.

For example, Micrococcal nuclease [(deoxy)ribonucleate-3'-nucleotidohydrolase, EC 3.1.4.7] can hydrolyze either ribonucleic acid (RNA) or deoxyribonucleic acid (DNA) to produce 3'-phosphomonunucleotides and dinucleotides. The enzyme is stable at pH between about 0.1 and 10 with maximum activity around pH 9 to 10 in the presence of 0.1-100 mM $Ca^{2+}$ ions. The gene encoding this enzyme has been isolated and characterized from *Staphylococcus aureus* (Shortle, *Gene* 22:181-89 (1983)) and is functionally expressed in a number of heterologous bacteria (Shortle, *Gene* 22:181-89 (1983); Miller, et al., *J. Bacteriol.* 169:3508-14 (1987); Liebl, et al., *J. Bacteriol.* 174:1854-61 (1992); LeLoir, et al., *J. Bacteriol.* 176:5135-39 (1996)).

The extracellular nuclease from *Serratia marcescens* is produced in a recombinant system available commercially as BENZONASE™ (Nycomed Pharma A/S and its affiliates, including American International Chemical Inc. (Natick, Mass.)). The gene encoding this enzyme also has been characterized (Ahrenholtz et al., *J. Bacteriol.* 60:3746-51 (1994)).

Methods of Engineering the Microbial Strains

Once the nuclease gene encoding the selected nuclease enzyme has been isolated and characterized, it is integrated into the microbial strain so that the organism will secrete nuclease into the periplasm or growth medium.

In a preferred embodiment, microbial strains for the production of short chain-length PHAs (*R. eutropha, E. coli*) or medium chain-length PHAs (*Pseudomonas* sp. MBX978 and *P. putida*) are generated by integrating a nuclease gene, such as the *S. aureus* nuclease gene, into the chromosome of PHA producing strains. For example, a nuclease encoding gene can be isolated from *S. aureus* by amplification using the polymerase chain reaction with oligonucleotides that recognize the nuclease encoding nuc gene. Following PCR, the amplified DNA can be cloned into the PCR cloning vector pCR2.1 (Invitrogen Corp., San Diego, Calif.). Plasmids containing the nuclease gene insert can be identified and analyzed for expression of nuclease using DNAse agar plates (Difco Laboratories, Detroit Mich.).

Several means are available for transferring the nuclease gene into the PHA production strain of choice for expression of the nuclease gene. For example, for transfer into *Ralstonia*, the gene can be put under the control of an *Ralstonia* promoter and inserted into a broad host range cloning vector, such as pLAFR3. A promoter and means for achieving expression in *Ralstonia* can be found in Peoples & Sinskey, *Mol. Microbiol.* (1989) and *J. Biol. Chem* 262, 15298-15303 (1989). Similar approaches using broad host range cloning vectors can be followed for bacterium from genera such as *Aeromonas, Azotobacter, Burkholderia, Comamonas, Methylobacterium. Paracoccus, Pseudomonas, Rhizobium,* and *Zoogloea*.

Alternatively, an expression cassette can be engineered for the nuclease such that it can be integrated into the chromosome of the appropriate host and expressed. Suitable expression cassettes are described, for example, in Herrero et al., *J. Bacteriol.* 172:6557-67 (1990). The nuclease gene and a marker gene, such as an antibiotic resistance-conferring gene, are cloned between the recognition sequences for a transposase in vectors such as the pUT and pLOF series (Herrero et al., *J. Bacteriol.* 172:6557-67 (1990)). When the pUT plasmids are used, transcriptional regulatory sequences do not need to be supplied in between the recognition sequences for the transposase, while with the pLOF series, these regulatory sequences are to be present within the region between the recognition sequences for the transposase. pUT and pLOF plasmids can only be maintained in *E. coli* strains that permit replication of this plasmid by virtue of the presence of a λ pir lysogen. The nuclease-marker construct is introduced into bacterial cells by conjugation from *E. coli*λ pir strains or by transformation or electroporation with plasmid DNA. In the absence of λ pir, the plasmid is lost from the cell. At a certain frequency, the DNA fragment enclosed by, and including, the recognition sequences for the transposase, will be transferred to the chromosome. Cells in which this event has occurred can be isolated by selection by plating the conjugation, transformation or electroporation mixture on solid growth media containing the antibiotic for which resistance is conferred by the construct. Colonies of cells growing on this medium are then screened for nuclease activity in vivo or in vitro. In vivo activity can be examined by plating the putative nuclease producers on DNase test agar plates using visualization with 1 N HCl or methyl green (Difco Laboratories, Detroit Mich.). In vitro activity can be determined by incubating culture supernatant or the aqueous supernatant of chloroform treated cells with high molecular weight DNA such as chromosomal DNA, followed by resolution of the DNA on pH buffered-agarose gels.

The utility of these engineered strains is readily evaluated by comparing the results of fermentation and downstream processes using the wild-type and the nuclease integrants.

Methods of Using the Engineered Strains

The engineered strains can be used in a variety of microbial fermentations utilized in the manufacture of pharmaceutical and industrial products, including antibiotics, organic acids, amino acids, proteins, vitamins, polyhydroxyalkanoates, and polysaccharides (Atkinson & Mavituna, "Biochemical Engineering and Biotechnology Handbook," $2^{nd}$ edition, (Stockton Press, USA 1991)). In a preferred embodiment, the fermentation process includes cell densities in excess of 100 g/L. The strains are particularly useful in processes in which the product must be recovered by cell lysis, and more particularly in processes that requires chromatography, crystallization, precipitation, centrifugation, and/or filtration separation processes.

In a preferred embodiment, the methods and strains described herein are used in fermentation processes for the production of PHAs, such as described, for example, in Lee & Chang, *Advances in Biochemical Engineering Biotechnology*, 52:27-58 (1995); Poirier et al., *Bio/Technology* 13:142-50 (1995); Doi, *Macromol Symp.* 98:585-99 (1995); U.S. Pat. No. 4,477,654 to Holmes et al., U.S. Pat. No. 5,364,778 to Byrom, U.S. Pat. No. 5,266,470 to Senior et al., U.S. Pat. No. 5,346,817 to Akiyama et al., U.S. Pat. No. 4,336,334 to Powell et al., U.S. Pat. No. 5,302,525 and U.S. Pat. No. 5,434,062 to Groleau et al., U.S. Pat. No. 5,292,860 to Shiotani et al., U.S. Pat. No. 5,059,536 and U.S. Pat. No. 5,096,819 to Page et al., U.S. Pat. No. 4,786,598 to Lafferty, U.S. Pat. No. 5,344,769 to Witholt et al., and U.S. Pat. No. 5,290,910 to Shiotani et al., U.S. Pat. No. 5,245,023 to Peoples et al., U.S. Pat. No. 5,334,520 to Dennis, U.S. Pat. No. 5,371,002 to Dennis et al., U.S. Pat. No. 5,512,456 to Dennis, U.S. Pat. No. 5,518,907 to Dennis et al., and U.S. Pat. No. 5,663,063 to Peoples et al.

In another preferred embodiment, the methods and strains described herein are used in the production of a highly pure PHA latex, which can have many applications. Examples of these applications are described in PCT WO 91/13207 (PHA latex compositions for coating paper); GB 2 292 648 A (PHA latex in architectural coating formulations); PCT WO 96/00263 (PHA latex as food, especially cheese, coatings); PCT WO 92/09211 and U.S. Pat. No. 5,229,158 to Yalpani (PHA granule compositions for use as dairy cream substitutes); PCT WO 92/09210 and U.S. Pat. No. 5,225,227 to Yalpani (PHAs as flavor delivery agents in foods); and PCT WO 96/17369 (PHAs used in the production of cathode ray tube components). It generally is necessary to lyse PHA-containing cells in order to obtain a PHA latex from the cells using an aqueous process. Methods for lysing microbial cells are well known and include physical homogenization, ultrasound waves, enzyme and detergent treatment, and freeze/thaw cycling.

In another preferred embodiment, the methods and engineered strains described herein are useful in the production of polysaccharides. Microbial polysaccharides can be produced by fermentation of a number of different microorganisms. For example, *Xanthomonas* strains are used commercially for the production of xanthan gum (Kennedy & Bradshaw, *Prog. Ind. Microbiol.* 19:319-71 (1984)), and *Pseudomonas elodea* strains are used to produce gellan gum (Kang, et al, *Appl. Environ. Micro.* 43: 1086-91 (1982)). Other examples include alginates, primarily from brown algae, which are used extensively in the food industry (Wells in *Extracellular Microbial Polysaccharides* (Sanford & Laskin, eds.) pp. 299 (ACS, Washington, D.C. 1977)). Alginates can also be produced by fermentation of *Azotobacter* strains (Chen et al., *Appl. Environ. Micro.* 49:543-46 (1985)). Hyaluronic acid is another example of a polymer which is produced for biomedical applications using Streptococci (Dougherty & van de Rijn, *J. Biol. Chem.* 269:169-75 (1994)).

The methods and systems described herein may be particularly advantageous when used in conjunction with the cell lysis approach to xanthan gum recovery described by Pollock in U.S. Pat. No. 5,354,671 and by Murofushi et al., in U.S. Pat. No. 5,705,368, and by Homma et al., in U.S. Pat. No. 5,679,556. Suitable *Xanthomonas* strains for practising the disclosed method are described by Bauer et al., in U.S. Pat. No. 4,400,467 and by Pollock et al., in U.S. Pat. No. 5,472,870.

A number of other microbial strains are used to produce polysaccharides and are amenable to the method disclosed herein. Genetic engineering techniques are now available for all of these microbes as described for example in Methods in Enzymology Volume 204, "Bacterial Genetic Systems: Miller, J. H. editor, Academic Press, New York. Cellulose production by *Acetobacter* is disclosed by Ben-Bassat et al., in U.S. Pat. No. 5,821,109 and by Tonouchi et al., for genetically engineered *Acetobacter* in U.S. Pat. No. 5,792,630. Exopolysaccharide production by *Zoogloea* and genetic engineering of this microbe is described by Easson et al., in U.S. Pat. No. 4,948,733 and U.S. Pat. No. 5,091,376. The microbial polysaccharide known as gellan gum is one member of a family of structurally related exopolysaccharides known as "sphingans' (Pollock, T. J. 1993, J. Gen. Microbiol. 139: 1939-1945, Pollock et. al., in U.S. Pat. No. 5,854,034 and references therein). Gellan gum is produced by *Pseudomonas elodea* (American Type Culture Collection strain Number ATCC 31461) by processes described in U.S. Pat. Nos. 4,326, 052; 4,377,636; 4,385,126 and 4,503,084. This strain and mutant derivatives with enhance gellan production characteristics can be genetically manipulated as described by Fialho et. al., 1991 Letters in Applied Microbiology 12: 85-87 and by Pollock et. al., in U.S. Pat. No. 5,854,034). For example, mutants of this strain deficient in the accumulation of PHB can also be used to practice the disclosed method and are available from The American Type Culture Collection as Strain Number ATCC 53967. Hyaluronic acid is produced by *Streptococcus* bacteria, as described, for example, by Ellwood et. al., U.S. Pat. No. 5,563,051.

The compositions and methods of preparation and use thereof described herein are further described by the following non-limiting examples.

Example 1

Isolation of the *Staphylococcus aureus* Nuclease Gene

Plasmid pNucl has been described in Liebl, et al., *J. Bacteriol.*, 174:1854-61 (1992)). The sequence of the nuc gene encoding micrococcal nuclease has been determined (Shortle, *Gene* 22:181-89 (1983)) and is accessible under GenBank Acc. No. J01785. The nuc gene was amplified using the purified plasmid pNucl and the polymerase chain reaction (PCR) with primers

```
SNS-Up
                                             (SEQ ID NO: 1)
(5'-TTCTCTAGAATTCAGGAGGTTTTTATGGCTATCAGTAATGTTTCG-
3')

and SNS-Dn
                                             (SEQ ID NO: 2)
(5'-GCCGGTACCTTATTGACCTGAATCAGCGTTG-3')
``` using the following conditions: 10 ng of pNucl DNA and 500 nM of each primer were mixed with 45 µl of PCR SuperMix (Gibco BRL, Gaithersburg, Md.) and amplified (2 min. 95° C., followed by 30 cycles of 30 sec. 95° C., 45 sec. 55° C., 45 sec. 72° C., and finally an extension step of 7 minutes at 68° C.). Following amplification by PCR, the 0.65 Kb containing the nuclease gene (SEQ ID NO:3) fragment was purified by agarose gel electrophoresis and ligated into the pCR2.1 cloning vector (Invitrogen, Carlsbad, Calif.) to obtain pCR2.1-nuc. The insert of this plasmid was confirmed by DNA sequencing as being identical to the corresponding region of that reported by Shortle (Shortle, 1993, Gene 22: 181-189).

Example 2

Construction of Transgenic *P. putida* KT2442 Strains Expressing a Nuclease

The nuc gene was excised from plasmid pCR2.1-nuc using restriction enzymes EcoRI and Acc65I and inserted in the corresponding sites of pUC18 NotI to obtain pUC18-nucI. A promoterless kanamycin gene from plasmid pBGS18 (Spratt et. al., 1986, Gene 41: 337-342; ATCC Accession Number 37437) was obtained by PCR amplification using the following primers:

```
linkK1
                                             (SEQ ID NO: 4)
5' TGTCTGCTTACATAAACAGTAATACAAAG 3', and linkK2,
                                             (SEQ ID NO: 5)
5' ATTTATTCAACAAAGCCGCC-3'
``` and the 0.9 Kb fragment (SEQ ID NO:6) inserted into the Ecl136II site of pUC18Not (Herrero et. al., 1990, *J. Bacteriol.* 172: 6557-6567) to obtain pMNx-kan. The promoterless kanamycin gene was excised by digestion with EcoRI and Acc651, blunt ended with klenow fragment of DNA polymerase and inserted into the SmaI site of pUC18nuc-1.

The resulting plasmid, pMNX-nuc, was linearized with SmaI and ligated with a blunt ended EcoRI/Acc65I fragment containing a promoterless kanamycin gene from pMNX-kan. Recombinant pMNX-nuc-kan plasmids were isolated based on their kanamycin resistance conferred by expression of the nuc-kan operon from the lac promoter. The nuc-kan operon subsequently was excised as a NotI fragment and inserted in the corresponding site of pUTkan. Plasmid pMUX-nuc-kan was subsequently used to integrate the promoterless nuc-kan operon randomly in the chromosomes of *P. putida* KT2442. Conjugation of the plasmid was achieved using *E. coli* S17-1 [pMUXnuc-kan].

Transgenic *P. putida* strains were selected on E2/10 mM octanoate/kanamycin/chloramphenicol plates. Out of 12,000 random integrants, 1500 colonies were replica plated to DNAse agar plates to select nuclease expressing clones. Thirty-five nuclease expressing clones were selected for in vitro analysis of nuclease levels in the culture supernatant and in the periplasm of the strain. For this purpose, cells were spun down and the supernatant containing the secreted nuclease was collected. The cell pellet subsequently was resuspended in fresh medium, and 100 µl of chloroform was added to 500 µl suspension to release periplasmic nuclease. Cell debris subsequently was spun down. DNA gel electrophoresis was conducted with samples treated with benzonase (0.02 U), with culture supernatant of nuclease integrated statlins, and with supernatant of *P. putida* KT2442. Nuclease activity in the secreted and periplasmic fractions of nine different *P. putida* nuc integrants on chromosomal DNA from *P. putida* KT2442 was present. Cell debris was Subsequently removed by centrifugation.

The presence of nuclease was determined by incubating aliquots of the clarified supernatant with 4 µg of *P. putida* chromosomal DNA for one hour at 37° C. As controls, chromosomal DNA was incubated with commercially available BENZONASE™, 0.02 units as a positive control or without nuclease as a negative control. Following digestion, the samples were analyzed by agarose gel electrophoresis (Sambrook et. al., 1989, Molecular Cloning, a Laboratory Manual, 2nd edition, Cold Spring Harbor Laboratory Press, Cold Spring Harbor, N.Y. Using this test, strains which express nuclease activity at different levels and extracellular or periplasmic space or both were readily identified.

These strains are called *P. putida* MBX918 through 926. *P. putida* MBX924 secretes nuclease to both periplasm and the extracellular medium and has the nuc-kan operon integrated in the 23S rRNA encoding gene.

Example 3

Construction of Transgenic R. eutropha 40124 Strains Expressing a Nuclease Gene Transgenic R. eutropha 40124 strains were selected after conjugation of the host strain with E. coli S17-1 [pMUX-nuc-kan] on PCT/1% glucose/naladixic acid/kanamycin plates. Ten random colonies were inoculated in PCT/1% glucose/naladixic acid/kanamycin liquid medium and grown for 20 hr. at 30° C. Only the R. eutropha MBX917 culture produced an active nuclease that was localized in the periplasm of the transgenic strain.

Example 4

Construction of Transgenic P. putida MBX978 Strains Expressing a Nuclease Gene Transgenic P. putida MBX978 strains were selected after conjugation of the host strain with E. coli S17-1 [pMUX-nuc-kan] on E2/10 mM octanoate/kanamycin/naladixic acid plates and subsequently replica plated on DNAse agar plates with the appropriate antibiotics. A total of 50 nuclease-positive colonies were replica plated to E2/10 mM octanoate/kanamycin/naladixic acid plates. Nine isolates (P. putida MBX979-987) subsequently were grown in liquid E2/10 mM octanoate/kanamycin/naladixic acid medium. All clones secrete nuclease activity into the periplasm. MBX984 secreted the highest levels of nuclease. All nine strains were tested in 50 ml E2/10 mM octanoate liquid medium for growth characteristics and PHA accumulation. Results are shown in Table 1 below. Cells were grown on E2 medium with 10 mM octanoate as carbon source. MBX985 retained the growing abilities and PHA accumulation activities of the wild-type strain.

TABLE 1

PHA Production by MBX978 Derivatives with an Integrated Nuclease Gene

| Strain | nuclease$^a$ | $OD_{600}$$^b$ | td (hr)$^c$ | PHA$^d$ |
|---|---|---|---|---|
| MBX978 | – | 3.7 | 1.5 | 34.3 |
| MBX979 | +++++ | 3.6 | 1.6 | 30.7 |
| MBX981 | + | 3.4 | 1.4 | 32.9 |
| MBX982 | ++ | 3.5 | 1.6 | 32.0 |
| MBX984 | ++++ | 2.8 | 1.6 | 14.9 |
| MBX985 | +++ | 3.8 | 1.4 | 33.2 |

$^a$relative nuclease avtivity;
$^b$optical density of the culture at 600 nm at the end of the experiment;
$^c$doubling time of the strain;
$^d$percentage PHA of the bacterial cell dry weight.

Example 5

Construction of Transgenic E. coli MBX247 Strains Expressing a Nuclease Gene Transgenic E. coli MBX247 strains were selected after conjugation of the host strain with E. coli S17-1 [pMUX-nuc-kan] on E2/10 mM octanoate/kanamycin/naladixic acid plates and subsequently replica plated on DNAse agar plates with the appropriate antibiotics. A total of 75 nuclease-positive colonies were replica plated to E2/10 mM octanoate/0.5% corn steep liquor/kanamycin/naladixic acid plates. Nine isolates were subsequently grown in liquid R10/2% glucose/kanamycin/naladixic acid medium. In four isolates, the nuclease gene was successfully integrated in the chromosome (MBX988-991). The nuclease activities in the different transgenic strains were analyzed. DNA gel electrophoresis was conducted with samples treated with periplasmic fractions of E. coli MBX247, E. coli MBX988 grown on R10 medium, E. coli MBX988 grown on LB medium, R. eutropha, MBX917, R. eutropha 40124, Pseudomonas MBX985, Pseudomonas MBX978, P. putida MBX924, P. putida KT2442, and with molecular weight markers.

The nuclease activities were analyzed in the different transgenic strains using the chromosomal DNA digestion and gele electrophoresis assay as described in Example 2.

These engineered strains were further modified by introducing genes encoding PHA biosynthetic enzymes, as described in U.S. Pat. Nos. 5,245,023; 5,334,520; 5,371,002; 5,512,456; 5,518,907; and 5,663,063.

Example 6

Isolation of PHA Granule Suspensions from P. putida MBX978 and a Nuclease Expressing Derivative P. putida MBX978 and P. putida MBX985 were grown to a cell density of 200 g/L in 20 L fed-batch cultures with octanoate as a carbon source. Following fermentation, each culture was supplemented with 1 mM $CaCl_2$ and adjusted to pH 8.5 with ammonium hydroxide. The cultures then were lysed using a high-pressure homogenizer operating at pressures varying from 8,000 to 20,000 psi. Each sample of lysate was incubated for one hour at room temperature, and then the viscosity was determined at 20° C. using a Brookfield LVF Viscometer (#1 spindle, 60 rpm). In addition to samples of wild-type and nuclease-expressing strains, lysates were prepared from wild-type culture supplemented with commercial nuclease (BENZONASE™, 10 µL/L culture). Results for the viscosity determinations are given in Table 2 and show that integration of the nuclease gene as in MBX985 resulted in reduced viscosity of the lysate to levels similar to that obtained for the wild-type strain with added benzonase.

TABLE 2

Disruption Pressures and Viscosities

| Disruption pressure (psi) | Viscosity (cP) | | |
|---|---|---|---|
| | MBX978 | MBX985 | MBX978 + BENZONASE ™ |
| 8000 | 48.0 | 9.5 | 9.0 |
| 12000 | 39.5 | 8.0 | 9.0 |
| 16000 | 38.0 | 8.0 | 8.0 |
| 20000 | 17.0 | 5.5 | 7.5 |

Modifications and variations of the present invention will be obvious to those of skill in the art from the foregoing detailed description. Such modifications and variations are intended to come within the scope of the following claims.

We claim:

1. A bacterial strain producing polyhydroxyalkanoates wherein the bacterial strain is selected from the group consisting of *Ralstonia eutropha, Pseudomonas putida* and *Escherichia coli* and is genetically modified to express a heterologous nuclease gene integrated into the chromosome of the bacterial strain, wherein the nuclease is secreted into the periplasmic space and released when the bacteria is lysed in an amount effective to degrade in less than 24 hours at least 95% of all of the nucleic acid released following lysis of the cells.

2. The bacterial strain of claim 1 which produces a polyhydroxyalkanoate to levels of at least 40% of its dry cell weight.

3. The bacterial strain of claim 1 for use in an aqueous process to manufacture poly(3-hydroxyalkanoate) granule suspension which is essentially free of nucleic acids.

4. The bacterial strain of claim 1 wherein the nuclease gene is a heterologous gene obtained from an organism other than the bacterial strain.

5. The bacterial strain producing polyhydroxyalkanoates of claim 1, wherein the bacterial strain is selected from the group consisting of *Ralstonia eutropha, Pseudomonas putida* and *Escherichia coli* and is genetically modified to express a heterologous nuclease gene integrated into the chromosome of the bacterial host, wherein the nuclease is secreted into the periplasmic space and released when the bacteria is lysed in an amount effective to degrade in less than 24 hours at least 95% of all of the nucleic acid released following lysis of the cells in a bacterial cell culture having a density of at least 50 g/l so that recovery of product is enhanced.

6. A fermentation process comprising
    adding to a growth medium a bacterial strain producing polyhydroxyalkanoates, wherein the bacterial strain is selected from the group consisting of *Ralstonia eutropha, Pseudomonas putida* and *Escherichia coli* and is genetically modified to express a heterologous nuclease gene integrated into the chromosome of the bacterial host, wherein the nuclease is secreted into the periplasmic space and released when the bacteria is lysed in an amount effective to degrade in less than 24 hours at least 95% of all of the nucleic acid released following lysis of the cells.

7. The process of claim 6, wherein the bacterial strain is grown to cell densities of at least 50 g/l.

8. The process of claim 7 further comprising growing the bacterial strain to produce levels of at least 40% of its dry cell weight.

9. The process of claim 6 further comprising lysing the cells.

10. The process of claim 8 further comprising using an aqueous process to manufacture a poly(3-hydroxyalkanoates) granule suspension which is essentially free of nucleic acids.

* * * * *